United States Patent
Avinash et al.

(10) Patent No.: US 10,475,217 B2
(45) Date of Patent: Nov. 12, 2019

(54) SYSTEMS AND METHODS FOR PROGRESSIVE IMAGING

(71) Applicant: General Electric Company, Schenectady, NY (US)

(72) Inventors: Gopal Biligeri Avinash, San Ramon, CA (US); Steven Michael Zanoni, Waukesha, WI (US); Saad Ahmed Sirohey, Pewaukee, WI (US); Vincent Adam, Buc (FR); Maud Bonnard, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 134 days.

(21) Appl. No.: 15/072,071

(22) Filed: Mar. 16, 2016

(65) Prior Publication Data

US 2017/0270695 A1  Sep. 21, 2017

(51) Int. Cl.
- *A61B 6/00* (2006.01)
- *G06T 11/00* (2006.01)
- *G06T 7/00* (2017.01)

(52) U.S. Cl.
CPC ............ *G06T 11/008* (2013.01); *A61B 6/463* (2013.01); *A61B 6/481* (2013.01); *A61B 6/486* (2013.01);
(Continued)

(58) Field of Classification Search
CPC .............. A61B 6/032; A61B 17/12109; A61B 17/12122; A61B 6/507; A61B 6/504;
(Continued)

(56) References Cited

U.S. PATENT DOCUMENTS

| 5,878,746 A | 3/1999 | Lemelson |
| 6,914,958 B2 * | 7/2005 | Ganin ............... A61B 6/032 378/26 |

(Continued)

OTHER PUBLICATIONS

Hopyan et al., Certainty of Stroke Diagnosis: Incremental Benefit with CT Perfusion over Noncontrast CT and CT Angiography, Apr. 2010 [retrieved Sep. 30, 2017], Radiology, vol. 255, No. 1, pp. 142-153. Retrieved from the Internet: http://pubs.rsna.org/doi/abs/10.1148/radiol.09091021.*

(Continued)

*Primary Examiner* — Matthew C Bella
*Assistant Examiner* — Dennis Rosario
(74) *Attorney, Agent, or Firm* — Dean D. Small; The Small Patent Law Group, LLC

(57) ABSTRACT

An imaging system includes an imaging unit, a display unit, and at least one processor. The at least one processor is configured to acquire a first type of diagnostic imaging information of the patient; reconstruct a first image using the first type of diagnostic imaging information; if a first stop criterion for terminating imaging is not satisfied, acquire a second type of diagnostic imaging information having an increased level of acquisitional burden; reconstruct a second image; if a second stop criterion for terminating imaging is not satisfied, acquire a third type of diagnostic imaging information having an increased level of acquisitional burden, wherein the patient is maintained on a table of the imaging unit during the acquisition of the second type of diagnostic imaging information, reconstruction of the second image, and acquisition of the third type of diagnostic imaging information; reconstruct a third image; and display the third image.

19 Claims, 8 Drawing Sheets

(52) U.S. Cl.
CPC .............. *A61B 6/504* (2013.01); *A61B 6/507* (2013.01); *A61B 6/5217* (2013.01); *A61B 6/54* (2013.01); *G06T 7/0012* (2013.01); *G06T 2207/10081* (2013.01); *G06T 2207/10141* (2013.01); *G06T 2207/30016* (2013.01); *G06T 2207/30104* (2013.01); *G06T 2211/404* (2013.01)

(58) Field of Classification Search
CPC ......... A61B 6/481; A61B 8/481; A61B 5/026; A61B 5/055; A61B 5/7285; A61B 6/541; A61B 8/543; A61B 6/463; A61B 2090/374; G06T 7/0012; G06T 2207/10081; G06T 2211/404; G06T 2207/30104; G06T 2207/10072; G06T 2207/30048; G06T 2207/10088; G06T 2207/30004; G06T 7/0016; G01R 33/5673; G01R 33/5635; G01R 33/5676
See application file for complete search history.

(56) References Cited

U.S. PATENT DOCUMENTS

| | | | | |
|---|---|---|---|---|
| 7,176,686 | B2* | 2/2007 | Katscher | G01R 33/5611 324/309 |
| 7,872,235 | B2 | 1/2011 | Rousso et al. | |
| 8,019,142 | B2* | 9/2011 | Nowinski | A61B 5/055 382/131 |
| 8,285,014 | B2* | 10/2012 | Lauritsch | A61B 6/4441 378/4 |
| 8,364,254 | B2 | 1/2013 | Jacquin | |
| 8,957,955 | B2* | 2/2015 | Reiner | G06F 17/3028 348/77 |
| 9,324,143 | B2* | 4/2016 | Goyal | A61B 6/507 |
| 9,326,702 | B2* | 5/2016 | Eichler | A61B 6/102 |
| 9,904,767 | B2* | 2/2018 | Desai | G16H 30/20 |
| 2004/0015337 | A1 | 1/2004 | Thomas et al. | |
| 2004/0121305 | A1 | 6/2004 | Wiegand et al. | |
| 2005/0215889 | A1 | 9/2005 | Patterson | |
| 2006/0100510 | A1* | 5/2006 | Klausz | A61B 6/032 600/429 |
| 2006/0160074 | A1 | 7/2006 | Dorn | |
| 2007/0081707 | A1 | 4/2007 | Sirohey | |
| 2007/0099239 | A1 | 5/2007 | Tabibiazar | |
| 2007/0100225 | A1* | 5/2007 | Maschke | A61B 6/032 600/407 |
| 2007/0198300 | A1 | 8/2007 | Duckert et al. | |
| 2007/0223796 | A1 | 9/2007 | Guehring | |
| 2008/0026485 | A1 | 1/2008 | Hueber | |
| 2011/0110486 | A1 | 5/2011 | Bouhnik et al. | |
| 2015/0282779 | A1* | 10/2015 | Deuerling-Zheng | A61B 6/504 600/427 |
| 2016/0317129 | A1* | 11/2016 | Seip | A61N 7/00 |

OTHER PUBLICATIONS

Struffert et al., Cerebral blood volume imaging by flat detector computed tomography in comparison to conventional multislice perfusion CT, Apr. 2011 [retrieved Sep. 22, 2018], European Radiology, vol. 22, Issue 4, pp. 882-889: Retrieved from the Internet: https://link.springer.com/article/10.1007/s00330-010-1957-6.*

Schramm et al., High-concentration contrast media in neurological multidetector-row CT applications: implications for improved patient management in neurology and neurosurgery, Jul. 2007 [retrieved Sep. 22, 2018], Neuroradiology, vol. 49, Supp. 1, pp. S35-S45. Retrieved from the Internet: https://link.springer.com/article/10.1007/s00234-007-1471-3.*

International Search Report and Written Opinion of the corresponding PCT application No. PCT/US2017/021153 dated Jun. 26, 2017, 18 total pages.

Enrique Marco De Lucas et al, "CT Protocol for Acute Stroke: Tips and Tricks for General Radiologists", Radiographics., vol. 28, No. 6, Oct. 1, 2008; pp. 1673-1687 (16 total pages).

Miles K A et al, "Perfusion CT: a Worthwhile enhancement?", British Journal of Radiology, London, GB, vol. 76, Apr. 1, 2003; pp. 220-231 (12 total pages).

* cited by examiner

SYSTEMS AND METHODS FOR PROGRESSIVE IMAGING

BACKGROUND OF THE INVENTION

The subject matter disclosed herein relates generally to systems and methods for imaging, such as computed tomography (CT) imaging, for example to systems and methods for progressive and/or value-based imaging.

Medical imaging may be used to help perform a diagnosis. Certain types of imaging may be completed relatively quickly and/or with relatively low dosage, but provide a relatively lower level of detail, while other types of imaging may be completed more slowly and/or with relatively high dosage, but provide a relatively higher level of detail. In some instances, it may not be known which type of imaging will provide the required level of detail for an accurate diagnosis. Conventionally, in such situations, a physician may order numerous different scans of different levels of detail to be performed, and analyze the results of each scan in attempting to make a diagnosis. However, such performance of a number of scans may result in unnecessary time and/or dosage spent performing scans that were not required for an accurate diagnosis.

BRIEF DESCRIPTION OF THE INVENTION

In one embodiment, an imaging system for progressively imaging a patient during a single patient visit is provided that includes an imaging unit of a first imaging modality, a display unit, and at least one processor. The at least one processor is operably coupled to the imaging unit and the display unit, and is configured to acquire a first type of diagnostic imaging information of the patient from the first imaging modality with the imaging unit. The at least one processor is also configured to reconstruct a first image using the first type of diagnostic imaging information and to display, via the display unit, the first image. If a first stop criterion for terminating imaging is not satisfied, the at least one processor is configured to acquire a second type of diagnostic imaging information of the first imaging modality with the imaging unit. The second type of diagnostic imaging information has an increased level of acquisitional burden relative to the first type of diagnostic imaging information. The at least one processor is further configured to reconstruct a second image using the second type of diagnostic imaging information, and to display, via the display unit, the second image. If a second stop criterion for terminating imaging is not satisfied, the at least one processor is configured to acquire a third type of diagnostic imaging information of the first imaging modality with the imaging unit. The third type of diagnostic imaging information has an increased level of acquisitional burden relative to the second type of diagnostic imaging information. The patient is maintained on a table of the imaging unit during the acquisition of the second type of diagnostic imaging information, reconstruction of the second image, and acquisition of the third type of diagnostic imaging information. The at least one processor is also configured to reconstruct a third image using the third type of diagnostic imaging information, and to display, via the display unit, the third image.

In another embodiment, a method (e.g., a method of progressively imaging a patient during a single patient visit) is provided that includes acquiring a first type of diagnostic imaging information of the patient from a first imaging modality with a first imaging unit. The method also includes reconstructing a first image using the first type of diagnostic imaging information, and analyzing the first image to determine if a first stop criterion for terminating imaging is satisfied by the first image. Responsive to a determination that the first stop criterion has been met, imaging is terminated. The method includes, responsive to a determination that the first stop criterion has not been met, acquiring a second type of diagnostic imaging information of the first imaging modality with the first imaging unit. The second type of diagnostic imaging information has an increased level of acquisitional burden relative to the first type of diagnostic imaging information. Also, the method includes reconstructing a second image using the second type of diagnostic imaging information, and analyzing the second image to determine if a second stop criterion for terminating imaging is satisfied by the second image. Responsive to a determination that the second stop criterion has been met, imaging is terminated. Responsive to a determination that the second stop criterion has not been met, the method further includes acquiring a third type of diagnostic imaging information of the first imaging modality with the first imaging unit. The third type of diagnostic imaging information has an increased level of acquisitional burden relative to the second type of diagnostic imaging information. The patient is maintained on a table of the first imaging unit during the acquiring the second type of diagnostic imaging information, reconstructing the second image, analyzing the second image, and acquiring the third type of diagnostic imaging information. Further, the method includes reconstructing a third image using the third type of diagnostic imaging information.

In another embodiment, a tangible and non-transitory computer readable medium is provided that includes one or more computer software modules configured to direct one or more processors to acquire a first type of diagnostic imaging information of the patient from a first imaging modality with a first imaging unit; reconstruct a first image using the first type of diagnostic imaging information; analyze the first image to determine if a first stop criterion for terminating imaging is satisfied by the first image; responsive to a determination that the first stop criterion has been met, terminate imaging; responsive to a determination that the first stop criterion has not been met, acquire a second type of diagnostic imaging information of the first imaging modality with the first imaging unit, the second type of diagnostic imaging information having an increased level of acquisitional burden relative to the first type of diagnostic imaging information; reconstruct a second image using the second type of diagnostic imaging information; analyze the second image to determine if a second stop criterion for terminating imaging is satisfied by the second image; responsive to a determination that the second stop criterion has been met, terminate imaging; responsive to a determination that the second stop criterion has not been met, acquire a third type of diagnostic imaging information of the first imaging modality with the first imaging unit, the third type of diagnostic imaging information having an increased level of acquisitional burden relative to the second type of diagnostic imaging information, wherein the patient is maintained on a table of the first imaging unit during the acquiring the second type of diagnostic imaging information, reconstructing the second image, analyzing the second image, and acquiring the third type of diagnostic imaging information; and reconstruct a third image using the third type of diagnostic imaging information.

DETAILED DESCRIPTION OF THE INVENTION

Figure 1:
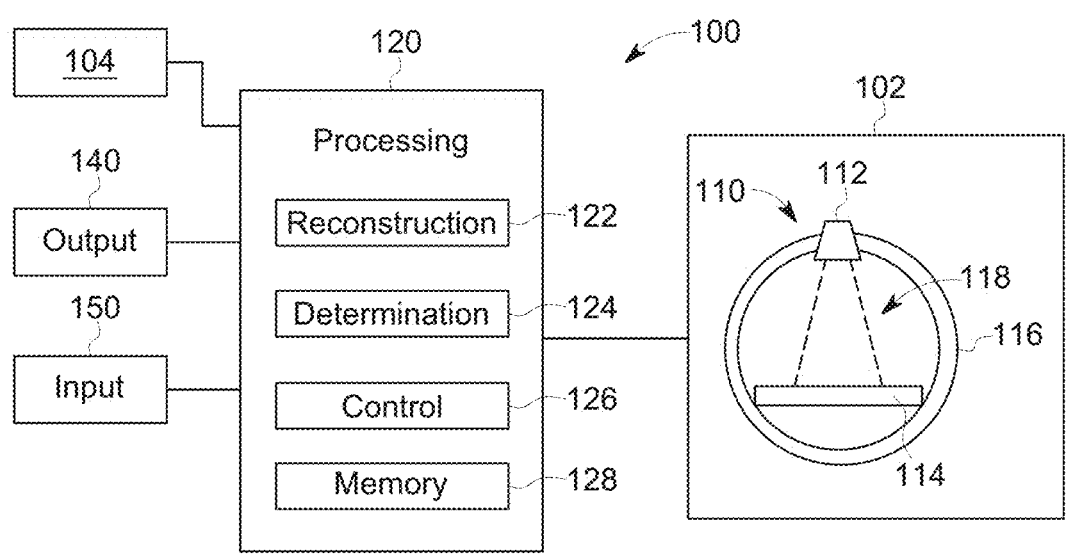
FIG. 1 is a schematic block diagram illustrating an imaging system in accordance with various embodiments.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and preceded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide systems and methods for progressive or value-based imaging. Some embodiments related to value based acquisition of medical images for suspected medical conditions of a patient. Various embodiments allow minimal image acquisition through a progressive refinement-based imaging process, while providing evidence (e.g., a displayed image) at each stage to allow a determination to stop further continued acquisition from that patient with a stopping criterion. Imaging information acquisition is continued until a stopping criterion is met. In some embodiments, the stopping criterion is determined using a processor programmed with analysis software coupled to an acquisition system that performs progressive analysis and provides visualization of the analysis results. For example, a human user may choose to stop additional imaging acquisition from the patient based on a displayed image and/or information relating to the displayed image (such as a quantitative measure determined using the displayed image). The progressive refinement-based imaging process may be configured to minimize acquisitional burden while providing progressively more detailed information for improved pathology detection rate. As used herein, acquisitional burden includes at least one of time required, dosage to patient, discomfort to patient, or inconvenience to patient. A varying trade-off between pathology detection rate, speed, and/or patient discomfort may be provided by the imaging process. For example, a first imaging process, for example, may minimize or reduce the time required for a scan, the dosage (radiation and/or contrast) provided to a patient, discomfort to the patient, and/or inconvenience to the patient, while providing a level of certainty for pathology detection. A second scan (and additional scans if appropriate), which may have increased time, dosage, and/or inconvenience, but also have an increased pathology detection rate relative to the first scan, may be performed if the results of the first scan do not provide sufficient certainty regarding a diagnosis.

In one example, imaging of a patient in connection with a stroke analysis is performed. First, non-contrast computed tomography (CT) is acquired. If, based on a non-contrast CT image, it is determined the patient is experiencing hemorrhagic stroke, the imaging process is stopped and surgery is performed to address the hemorrhagic stroke. If the non-contrast CT image does not indicated hemorrhagic stroke, then a subsequent imaging step of acquiring multi-phase CT information is performed, and an image reconstructed using the multi-phase CT information is analyzed to determine if stop criterion (e.g., sufficient collateral filling to permit immediate removal of a clot). If the stop criterion is satisfied, the imaging may be terminated and the patient transferred for surgery. If the stop criterion is not satisfied (e.g., if it is not determinable from the image whether or not there is sufficient collateral filling), the progressive imaging may proceed to acquire CT perfusion imaging data. If the stop criterion is not met following CT perfusion imaging, for example, in some embodiments the progressive imaging may proceed to acquire MR perfusion imaging information.

In another example, an imaging sequence or process may begin with a low dose, thick slice, large coverage CT scan in a first scan for quick assessment of a larger area. A subsequent scan (or scans) may be progressively targeted on a smaller FOV (e.g., an identified lesion and/or particular anatomy) using thinner slices and/or higher dosage.

Generally, in various embodiments, a first type or genre of data of a first modality is acquired, and it is determined if a stop criteria is satisfied after acquiring the first type or genre of data. If the stop criterion is met, no further imaging is performed, but if the stop criterion is not met, a progressively refined second genre of type of data of the first modality (e.g., a more detailed and/or complex type of scan) is performed. As long as stop criteria are not met, the process may be continued by acquiring different genres or types of progressively refined data of the first modality. In some embodiments, after a given number of types of images of a first modality have been reconstructed without satisfying a stop criterion, one or more genres or types of scans of a second imaging modality may be performed. The type of scan and/or modality of scan may be updated until a stop criterion is met or satisfied.

Various embodiments provide improved imaging. A technical effect of at least one embodiment includes reduced number of scans (e.g., by eliminating unnecessary subsequent scans when enough information is available from a previous scan). A technical effect of at least one embodiment includes reduced radiation dose (e.g., by eliminating unnecessary subsequent scans when enough information is available from a previous scan). A technical effect of at least one embodiment includes improved efficiency of performing a series of scans (e.g., by analyzing a previous scan while preparing a subsequent scan). A technical effect of at least one embodiment is to provide images for use in accurate diagnosis of medical conditions such as stroke. A technical effect of at least one embodiment includes reduction of delay between scanning and performing a medical procedure.

FIG. 1 illustrates an imaging system 100 in accordance with an embodiment. The imaging system 100 may be configured, for example, to perform progressive or value-based imaging of a patient using one or more imaging modalities (e.g., computed tomography (CT), X-ray, magnetic resonance imaging (MRI), ultrasound, photon emission tomography (PET), single photon emission computed tomography (SPECT)). The illustrated embodiment, for example, includes a first imaging unit 102 of a first modality, and a second imaging unit 104 of a second modality, as well as a processing unit 120, an output unit (or display) 140, and an input unit 150. For example, the first modality may be CT and the second modality may be MRI. Additional or alternative modality imaging units may be used in various embodiments. Generally, the imaging system 100 is configured to progressively image a patient. The imaging system 100 is configured to acquire a series of image datasets, with each subsequent image dataset requiring more acquisitional burden and/or providing additional diagnostic detail than a preceding image dataset. Before proceeding to perform the next imaging scan in a series, the imaging system 100 (e.g., processing unit 120 either automatically and/or with use of user input) determines if a stop criterion has been reached. If, based on an analysis of an already obtained image, a stop criterion is met, the progressive imaging process is terminated, avoiding more complex imaging scans that take additional time and/or subject the patient to additional dosage (e.g., radiation dosage, contrast dosage). If, however, the stop criterion has not been reached (e.g., the already obtained scans do not provide sufficient information from which to make a diagnostic decision), a subsequent, more detailed, burdensome, and/or complex imaging scan is performed.

As one example, the imaging system may be utilized as part of an analysis of a stroke patient. A first scan may be performed to determine if the patient is experiencing a hemorrhagic stroke or an ischemic stroke. If, based on an image reconstructed using information acquired during the first scan, it is determined that the stroke is hemorrhagic, further scans are not performed, and the patient may be treated for the hemorrhagic stroke. If, however, the stroke is determined to be ischemic, one or more subsequent scans may be performed until an image is obtained from which it is determined whether collateral filling is sufficient to allow for a surgical procedure to remove an identified clot.

Generally, the first imaging unit 102 and the second imaging unit 104 are configured to acquire projection data or imaging data (e.g., CT data or CT imaging information), and the processing unit 120 is configured to reconstruct images using the data acquired by one or more of the imaging units. It may be noted that various embodiments may include additional components, or may not include all of the components shown in FIG. 1 (for example, various embodiments may provide sub-systems for use with other sub-systems to provide an imaging system; various embodiments may only include the first imaging unit 102 of the first modality). Further, it may be noted that certain aspects of the imaging system 100 shown as separate blocks in FIG. 1 may be incorporated into a single physical entity, and/or aspects shown as a single block in FIG. 1 may be shared or divided among two or more physical entities.

The depicted first imaging unit 102 includes a CT acquisition unit 110 which in turn includes an X-ray source 112 and a CT detector 114. (For additional information regarding example CT systems, see FIG. 8 and related discussion herein.) The X-ray source 112 and the CT detector 114 (along with associated components such as bowtie filters, source collimators, detector collimators, or the like (not shown in FIG. 1)) may rotate about a central axis of a bore of a gantry 116 of the system 100.

Generally, X-rays from the X-ray source 112 may be guided to an object to be imaged through a source collimator and bowtie filter. The object to be imaged, for example, may be a human patient or a portion thereof (e.g., head or torso, among others). The source collimator may be configured to allow X-rays within a desired field of view (FOV) to pass through to the object to be imaged while blocking other X-rays. The bowtie filter module may be configured to absorb radiation from the X-ray source 112 to control distribution of X-rays passed to the object to be imaged.

X-rays that pass through the object to be imaged are attenuated by the object and received by the CT detector 114 (which may have a detector collimator associated therewith), which detects the attenuated X-rays and provides imaging information to the processing unit 120. The processing unit 120 may then reconstruct an image of the scanned portion of the object using the imaging information (or projection information) provided by the CT detector 114. The processing unit 120 includes or is operably coupled to the output unit 140, which in the illustrated embodiment is configured to display an image, for example, an image reconstructed by the processing unit 120 using imaging information from the CT detector 114. The depicted input unit 150 is configured to obtain input corresponding to a scan to be performed, with the processing unit 120 using the input to determine one or more scan settings (e.g., tube voltage, tube current, scanning rotation speed, or the like). The input unit 150 may include a keyboard, mouse, touchscreen or the like to receive input from an operator, and/or may include a port or other connectivity device to receive input from a computer or other source.

In the illustrated embodiment, the X-ray source 112 is configured to rotate about the object. For example, the X-ray source 112 and the CT detector 114 may be positioned about a bore 118 of the gantry 116 and rotated about the object to be imaged. As the X-ray source 112 rotates about the object during an imaging scan, X-rays received by the CT detector 114 during one complete rotation provide a 360 degree view of X-rays that have passed through the object. Other imaging scanning ranges may be used in alternative embodiments. The CT imaging information may be collected as a series of views that together make up a rotation or portion thereof. A blanking interval for may separate a first view or projection from the next view or projection in the series.

As indicated herein, the processing unit 120 is configured to control various aspects of the acquisition units and/or to reconstruct an image using information obtained via the acquisition units. For example, the processing unit 120 may be configured to reconstruct a CT image (or a series of CT images using information acquired at different times) using information collected by the CT acquisition unit 110.

The depicted processing unit 120 is operably coupled to the input unit 150, the output unit 140, the first imaging unit 102, and the second imaging unit 104. The processing unit 120, for example, may receive information regarding a scan from the input unit 150 that may be utilized in determining scanning parameters to be used in acquiring CT imaging information. The processing unit 120 in various embodiments receive user inputs from the input unit 150 that correspond to satisfaction (or lack thereof) of a stop criterion (e.g., whether information is sufficient from an already performed scan to make performance of a subsequent scan or scans necessary or desirable). As another example, the processing unit 120 may receive imaging data or projection data from the imaging units (e.g., CT detector 114). As one more example, the processing unit 120 may provide control signals to one or more aspects of the imaging units, such as the CT acquisition unit 110, for example the X-ray source 112 and CT detector 114. The processing unit 120 may include processing circuitry configured to perform one or more tasks, functions, or steps discussed herein. It may be noted that "processing unit" as used herein is not intended to necessarily be limited to a single processor or computer. For example, the processing unit 120 may include multiple processors and/or computers, which may be integrated in a common housing or unit, or which may distributed among various units or housings.

The depicted processing unit 120 is configured to control the first imaging unit 102 and the second imaging unit 104 to acquire imaging information. For example, the depicted processing unit 12 is configured to control the CT acquisition unit 110 (e.g., by controlling the activation and deactivation of the X-ray source 112) to collect CT imaging information during an imaging scan. The processing unit 120 in the illustrated embodiment is configured to control the CT acquisition unit 110 to acquire different types of imaging information using different scan procedures. For example, the depicted processing unit 120 is configured to control the CT acquisition unit 110 to perform non-contrast CT imaging scans, multi-phase CT imaging scans, and CT perfusion imaging scans.

In the embodiment depicted in FIG. 1, the processing unit includes a reconstruction module 122, a determination module 124, a control module 126, and a memory 128. It may be noted that other types, numbers, or combinations of modules may be employed in alternate embodiments, and/or various aspects of modules described herein may be utilized in connection with different modules additionally or alternatively. Generally, the various aspects of the processing unit 120 act individually or cooperatively with other aspects to perform one or more of the methods, steps, or processes discussed herein (e.g., method 200 or aspects thereof).

The depicted reconstruction module 122 is configured to reconstruct one or more images using imaging or projection data acquired from the first imaging unit 102 and/or the second imaging unit 104 (e.g., from the CT detector 114 of the first imaging unit 102). For example, the reconstruction module 122 may receive imaging information from the CT detector 114 taken over a number of views (e.g., for a full rotation or portion thereof, or for a number of rotations taken at different positions along the length of an object to be imaged) and reconstruct an image used for diagnostic purposes.

In the illustrated embodiment, the determination module 124 is configured to receive information from the first imaging unit 102 and/or the second imaging unit 104 (e.g., CT imaging information from the CT acquisition unit 110), and/or information from the reconstruction module 122 (e.g., a reconstructed image) and/or the input unit 150 (e.g., information corresponding to a stop criterion, such as a user input indicating satisfaction or dissatisfaction of a stop criterion), and to determine, for example, whether a stop criterion has been satisfied or whether a subsequent scan should be performed. In some embodiments, the determination module 124 determines the type of subsequent scan to be performed.

For example, the determination module 124 may first determine if a stop criterion has been satisfied. In some embodiments, the determination module 124 determines if a stop criterion is satisfied based on an objective or measurable parameter (or parameters) automatically determined via analysis of a reconstructed image. In some embodiments, the determination module 124 determines if a stop criterion is satisfied based on receipt (or failure to receive) a user input. For instance, in some embodiments, the determination module 124 (or other aspect of processing unit 120) determines that a given stop criterion is not satisfied if an input corresponding to a satisfaction of the given stop criterion is not received within a predetermined amount of time after displaying a corresponding image. For example, after display of a given reconstructed image, the determination module 124 may begin a timing period. If no input is received from an operator before expiration of the timing period, the determination module 124 determines that the stop criterion has not been satisfied, and the processing unit 120 controls the imaging system 100 to acquire the next, more detailed or complex imaging scan in a series.

In one example scenario, a patient experiencing a stroke may be diagnosed using a progressive imaging process using the imaging system 100. In the example scenario, a sequence of up to three CT imaging scans are performed, with each subsequent scan having additional acquisitional burden relative to the preceding scan, as necessary. The first imaging scan is a non-contrast CT imaging scan, the second imaging scan is a multi-phase CT imaging scan, and the third imaging scan is a perfusion CT imaging scan. A different stop criterion is employed for the first and second scans.

In the example scenario, after the CT imaging information has been collected with the CT acquisition unit 110, the reconstruction module 122 reconstructs a non-contrast image, and the image (which may have undergone postprocessing to assist in diagnosis) is displayed via the output unit 140. The stop criterion for the first scan in the example scenario corresponds to a determination of a level of bleeding corresponding to hemorrhagic stroke. The satisfaction of the stop criterion in the example scenario is based on a user input. If a user provides an input to the input unit 150 indicating that an amount of bleeding corresponding to hemorrhagic stroke has been determined based on the displayed image, the determination module 124 determines that a stop criterion has been met and no further scans are performed. Instead, the patient may be treated for hemorrhagic stroke without further delay for additional scans. If, however, the user provides an input indicating that an amount of bleeding corresponding to hemorrhagic stroke has not been identified (or fails to provide an input within a predetermined time period), the determination module 124 determines that a stop criterion has not been satisfied, and a subsequent scan is performed.

In the example scenario, the subsequent scan is a multi-phase CT angiography (CTA) exam. A contrast agent is introduced to the patient, and the CT acquisition unit 110 acquires multi-phase CTA imaging information. Multi-phase CTA provides temporal information regarding blood vessels, for example that may be used to help determine an extent of arterial filling in the brain for ischemic stroke patients. If sufficient arterial filling is determined, a clot may be identified and removed; however, if filling is insufficient, there may be a risk of blood vessel rupture due to pressure change after removal of a clot. After the CT imaging information has been collected with the CT acquisition unit 110, the reconstruction module 122 reconstructs an image or images (e.g., one or more images corresponding to vessels of the brain at different phases or points in time), and the image (which may have undergone postprocessing to assist in diagnosis) is displayed via the output unit 140. The stop criterion for the second scan in the example scenario corresponds to a determination of a sufficient level of collateral filling of blood vessels (e.g., a sufficient level to permit removal of a clot without undue risk of vessel rupture). The satisfaction of the second stop criterion in the example scenario is based on a user input. If a user provides an input to the input unit 150 indicating that a sufficient level of collateral filling has been determined based on the displayed image, the determination module 124 determines that a stop criterion has been met and no further scans are performed. Instead, the patient may be treated for ischemic stroke (e.g., removal of a clot) without further delay for additional scans. If, however, the user provides an input indicating an insufficient level of collateral filling or an inability to determine whether or not a sufficient level of collateral filling exists (or the user fails to provide an input within a predetermined time period), the determination module 124 determines that a stop criterion has not been satisfied, and a subsequent scan is performed.

In the example scenario, the subsequent scan is a CT perfusion exam. After the contrast agent associated with the multi-phase CTA exam has sufficiently washed out, a different contrast agent is introduced to the patient for CT perfusion analysis, and the CT acquisition unit 110 acquires CT perfusion imaging information. Multi-phase CTA provides information regarding brain tissue and whether sufficient blood flow is being provided to keep tissue alive. If multi-phase CTA imaging information was not sufficient to determine whether or not collateral filling was sufficient, CT perfusion information may be acquired to better determine whether or not collateral filling was sufficient.

It may be noted that the various imaging scans in a progressive series of scans may have corresponding scanning parameters or settings (e.g., parameters or settings used to acquire information) as well as display parameters or settings (e.g., parameters or settings used in postprocessing for convenient display). In some embodiments, the determination module 124 (and/or other aspect or portion of the processing unit 120) determines a subsequent type of scan to be performed, as well as scanning and display parameters. For example, in some embodiments, for a progressive stroke imaging sequence, if a stop criterion is not satisfied after analysis of a non-contrast CT image, the determination module 124 determines that a multi-phase CTA imaging scan is to performed, and directs to the control module 124 to use appropriate settings for multi-phase CTA image acquisition. Further, the determination module 124 determines that a postprocessing routine tailored for use with multi-phase CTA is to be used, and provides the appropriate information to the reconstruction module 122 (or other aspect of the processing unit 120) for use in postprocessing and displaying an image reconstructed using the multi-phase CTA imaging information.

In the illustrated embodiment, the determination module 124 is communicably coupled to the control module 126, with the control module 126 configured to control the first imaging unit 102 and/or the second imaging unit 104 (e.g., the CT acquisition unit 110 and/or other aspects of the system 100), and to perform the imaging scans called for by the determination module 124.

The output unit 140 is configured to provide information to the user. The output unit 140 is configured to display, for example, an image (e.g., an image that has been reconstructed and postprocessed as discussed herein). Additionally, the output unit 140 may provide, among other things, guidance regarding determination of a stop criterion, display a timer indicating when the determination module 124 will determine failure to satisfy satisfaction of stop criterion absent a contrary input, measured or determined parameters corresponding to a displayed image. The output unit 140 may include one or more of a screen, a touchscreen, a printer, or the like.

The input unit 150 may be configured to obtain an input that corresponds to one or more settings or characteristics of a scan or progressive series of scans to be performed, and to provide the input (or information corresponding to the input) to the processing unit 120, which may use the input to determine, adjust, or select settings used to acquire imaging information, reconstruct imaging information, postprocess or otherwise prepare one or more images for display, or the like. For example, the input unit 150 may receive an instruction specifying a procedure, and the processing unit then determines the appropriate sequence of scans and corresponding reconstruction and postprocessing routines. The input may include, for example, a type of progressive imaging to perform, such as stroke analysis. Responsive to receiving the input from the input unit 150, the processing unit 120 automatically initiates a corresponding series of scans, which may be selectively performed until a stop criterion is satisfied. The input unit 150 may be configured to accept a manual user input, such as via a touchscreen, keyboard, mouse, or the like. Additionally or alternatively, the input unit 150 may receive information from another aspect of the imaging system 100, another system, or a remote computer, for example, via a port or other connectivity device. In various embodiments, the input unit 150 also receives input regarding criteria satisfaction. In some embodiments, a user may provide input, based on visual inspection of a displayed image, whether or not a stop criterion is satisfied (and/or whether the image does not provide enough information to make a determination). In some embodiments, a user may provide an indication if a stop criterion is satisfied, and the processing unit 120 may automatically proceed to a next scan in a series if no input is received within a predetermined time period. Use of a predetermined time period for automatically advancing to a subsequent imaging stage reduces the amount of time taken for a series of scans in various embodiments.

Figure 2:
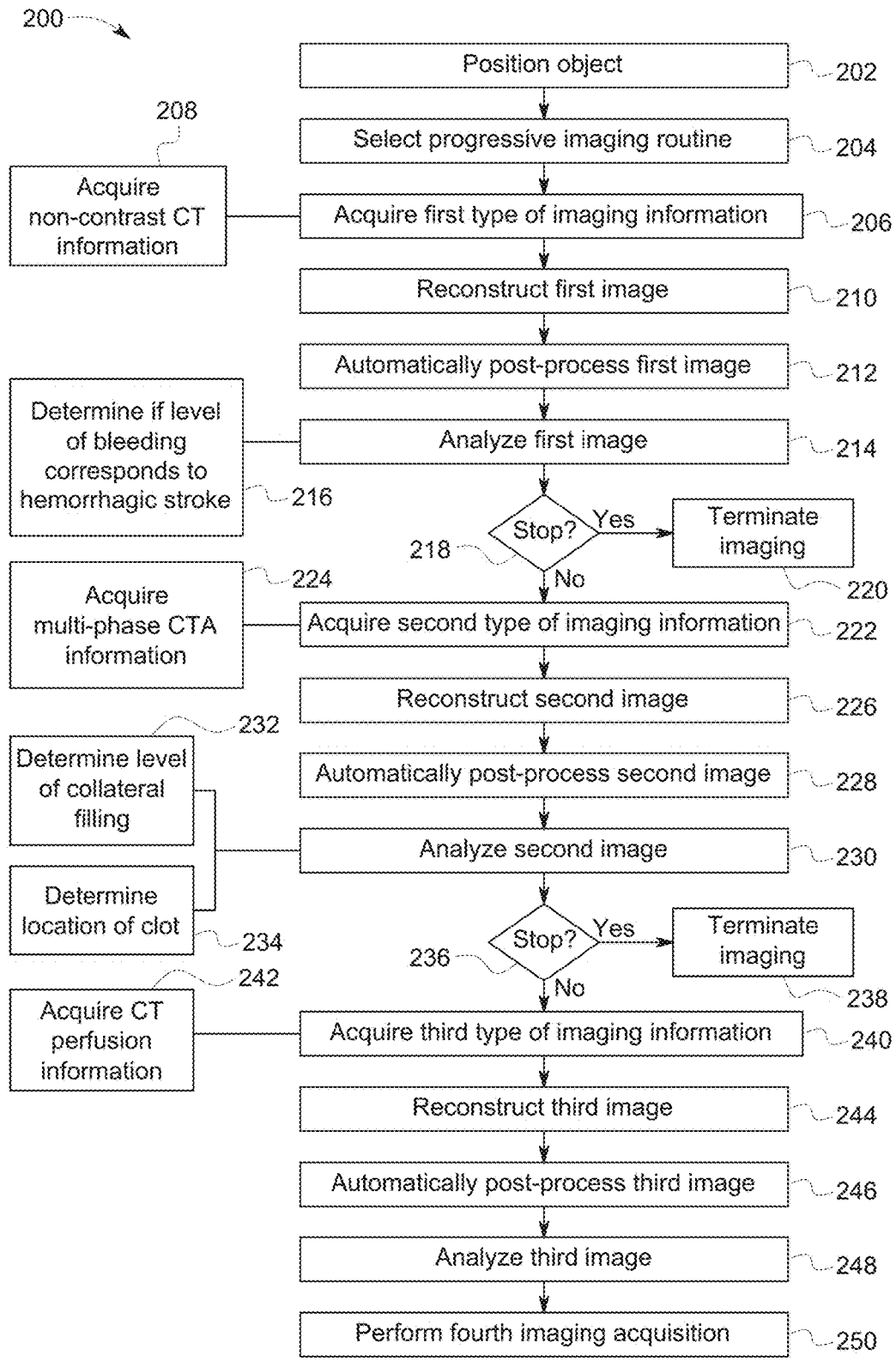
FIG. 2 is a flowchart of a method in accordance with various embodiments.

FIG. 2 provides a flowchart of a method 200 for progressively imaging an object, for example a patient as part of a stroke analysis, in accordance with various embodiments. The method 200, for example, may employ or be performed by structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 200 may be able to be used as one or more algorithms to direct hardware (e.g., one or more aspects of the processing unit 120) to perform one or more operations described herein.

At 202, the object (e.g., patient is positioned). For example, the object may be a human patient positioned on a table in a bore of an imaging system (e.g., first imaging unit 102 or second imaging unit 104), which may include, for example, a CT acquisition unit (e.g., CT acquisition unit 110).

Figure 3:
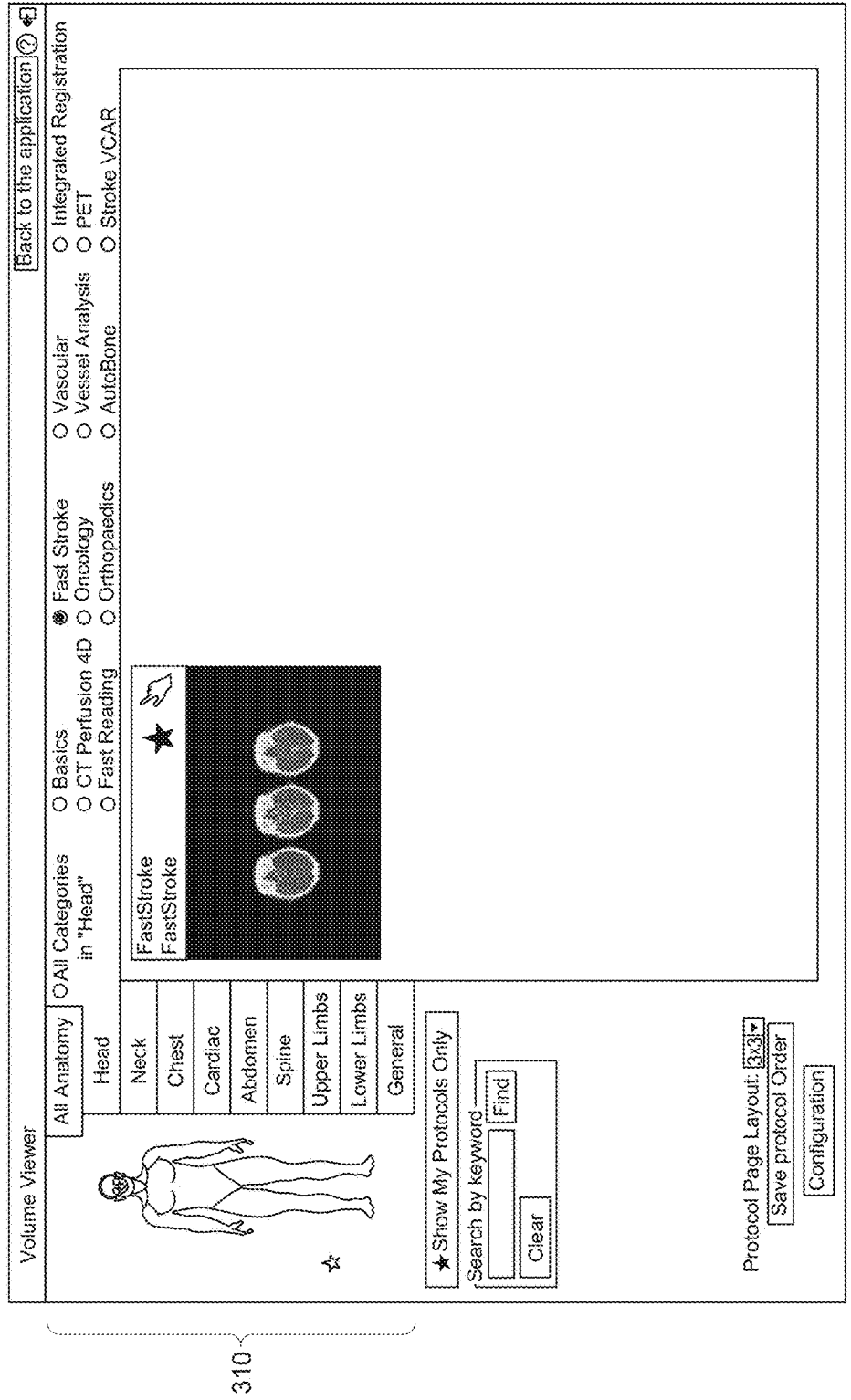
FIG. 3 illustrates an example display in accordance with various embodiments.

At 204, a progressive imaging routine or procedure is selected. The progressive imaging routine in various embodiments specifies a series of scans of increasing acquisitional burden or detail that are performed to aid in diagnosis of a condition. For example, for a stroke diagnosis progressive imaging routine, a series of scans may include a non-contrast CT scan, a multi-phase contrast CTA scan, and a CT perfusion scan. The progressive imaging routine may be selected or determined based on a user input provided to processing unit (e.g., to processing unit 120 via input unit 150). FIG. 3 provides an example illustration of a display 300 in accordance with various embodiments which a user may use to provide an input to select a progressive imaging routine. The display 300 includes various user guidance features 310, which allow a user to specify a portion of the body to be scanned. As seen in FIG. 3, the depicted display also includes user selection buttons 320 corresponding to available scanning procedures. In the illustrated embodiment, the user has selected "Fast Stroke." Responsive to the user selection, a processing unit may prepare a system to perform the series of scans using predetermined acquisition, reconstruction, and display parameters for the selected routine.

At 206, a first type of imaging information is acquired. For example, the first type of imaging information in various embodiments is acquired using a first modality of a first imaging unit. In some embodiments, the first type of imaging information is non-contrast information. In some embodiments, an X-ray source and detector may be rotated about the object being imaged and operated in a manner prescribed by predetermined scanning parameters to collect imaging information at a detector. As one example, in the illustrated embodiment, at 208, the first type of diagnostic imaging information is non-contrast CT (e.g., acquired via CT acquisition unit 110), and the first stop criterion is a determination of a level of bleeding corresponding to hemorrhagic stroke.

Figure 4:
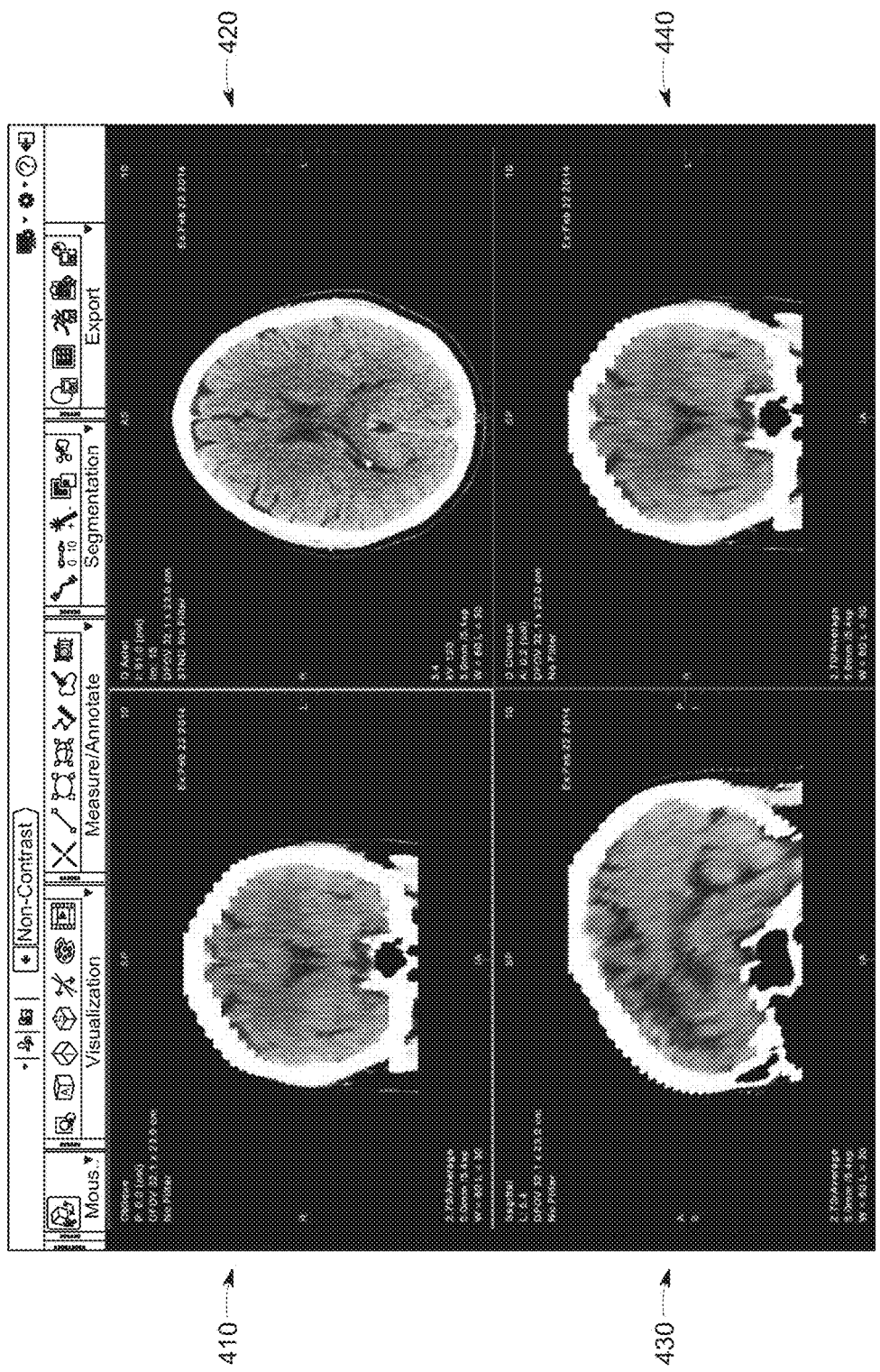
FIG. 4 illustrates an example display in accordance with various embodiments.

At 210, a first image is reconstructed. The first image is reconstructed using the first imaging information acquired at 206. At 212, the reconstructed image is automatically postprocessed. For example, in various embodiments, a processing unit (e.g., processing unit 120) may postprocess the reconstructed first image using a predetermined postprocessing routine based on the selected progressive imaging routine to provide a user with a convenient, easily usable display for determining if a stop criterion is satisfied. FIG. 4 illustrates an example non-contrast CT display 400 in accordance with various embodiments. The display 400 includes four views (namely, an oblique view 410, an axial view 420, a sagittal view 430, and a coronal view 440) which may be used by a viewer of the display to determine if there is a level of bleeding corresponding to hemorrhagic stroke present or not.

At 214, the first image is analyzed to determine if a first stop criterion for terminating imaging is satisfied by the first image. The analysis in some embodiments may be performed by an operator or user viewing an image on a display (e.g., display unit 140). It may be noted that the display may be remote from other aspects of an imaging system, so that a physician not present at a scanning facility may determine if a stop criterion has been satisfied. In some embodiments, a processing unit (e.g., processing unit 120) may be configured to analyze one or more determinable parameters or objective measurements corresponding to a reconstructed image to determine if a stop criterion has been met. In the depicted embodiment, at 216, the first image is analyzed to determine if a level of bleeding corresponding to hemorrhagic stroke is present.

At 218, it is determined if the first stop criterion has been met or satisfied. Generally, if a stop criterion is met, the progressive imaging routine may be terminated before performing additional, more complex scans that are unnecessary if an earlier scan provides sufficient information for a particular diagnosis. If the first stop criterion is met, the method 200 proceeds to 220 and the imaging series is terminated. If the stop criterion is not met or satisfied, the method proceeds to 222. For example, if a level of bleeding consistent with hemorrhagic stroke is present, the patient may be transferred from the imaging device for treatment of the hemorrhagic stroke immediately, without spending additional time performing scans. If, however, the level of bleeding does not correspond to hemorrhagic stroke, an ischemic stroke may be diagnosed, for which additional imaging will be beneficial, for example, to determine a location of a clot as well as the extent of collateral filling.

At 222, a second type of diagnostic imaging information is acquired. For example, in various embodiments, the second type of diagnostic imaging information is of the same, first modality as the first type of diagnostic imaging information, is acquired with the same, first imaging unit, and has an increased level of acquisitional burden relative to the first type of diagnostic imaging information. In some embodiments, the second type of imaging information is multi-phase information. For example, in the illustrated embodiment, at 224, the second type of diagnostic imaging information is multi-phase CTA information, and the second stop criterion is determination of a sufficient level of collateral filling of blood vessels. In the illustrated embodiment, a contrast agent is introduced in the patient before acquiring CT information as part of a multi-phase CTA imaging process.

Figure 5:
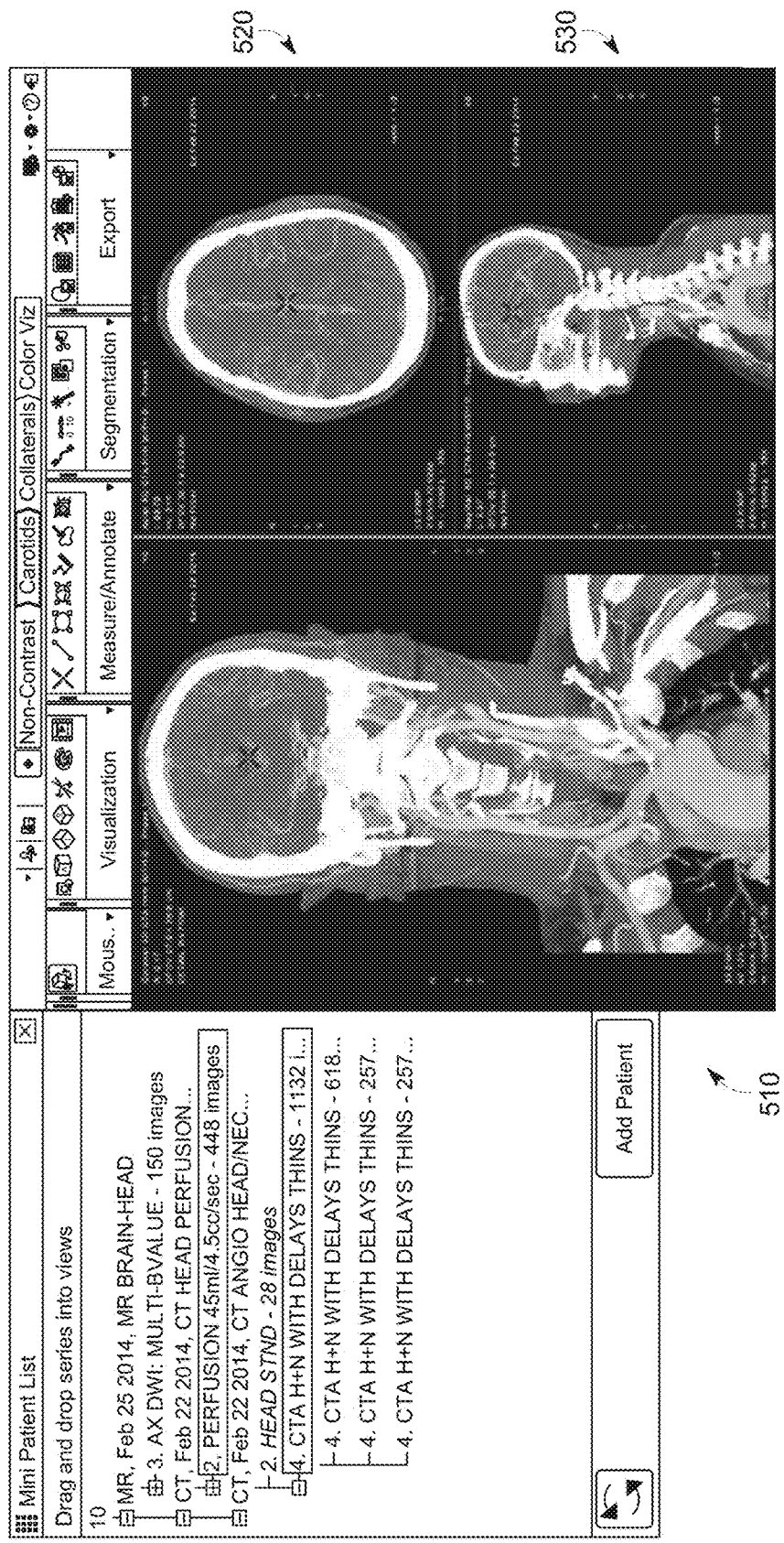
FIG. 5 illustrates an example display in accordance with various embodiments.
Figure 6:
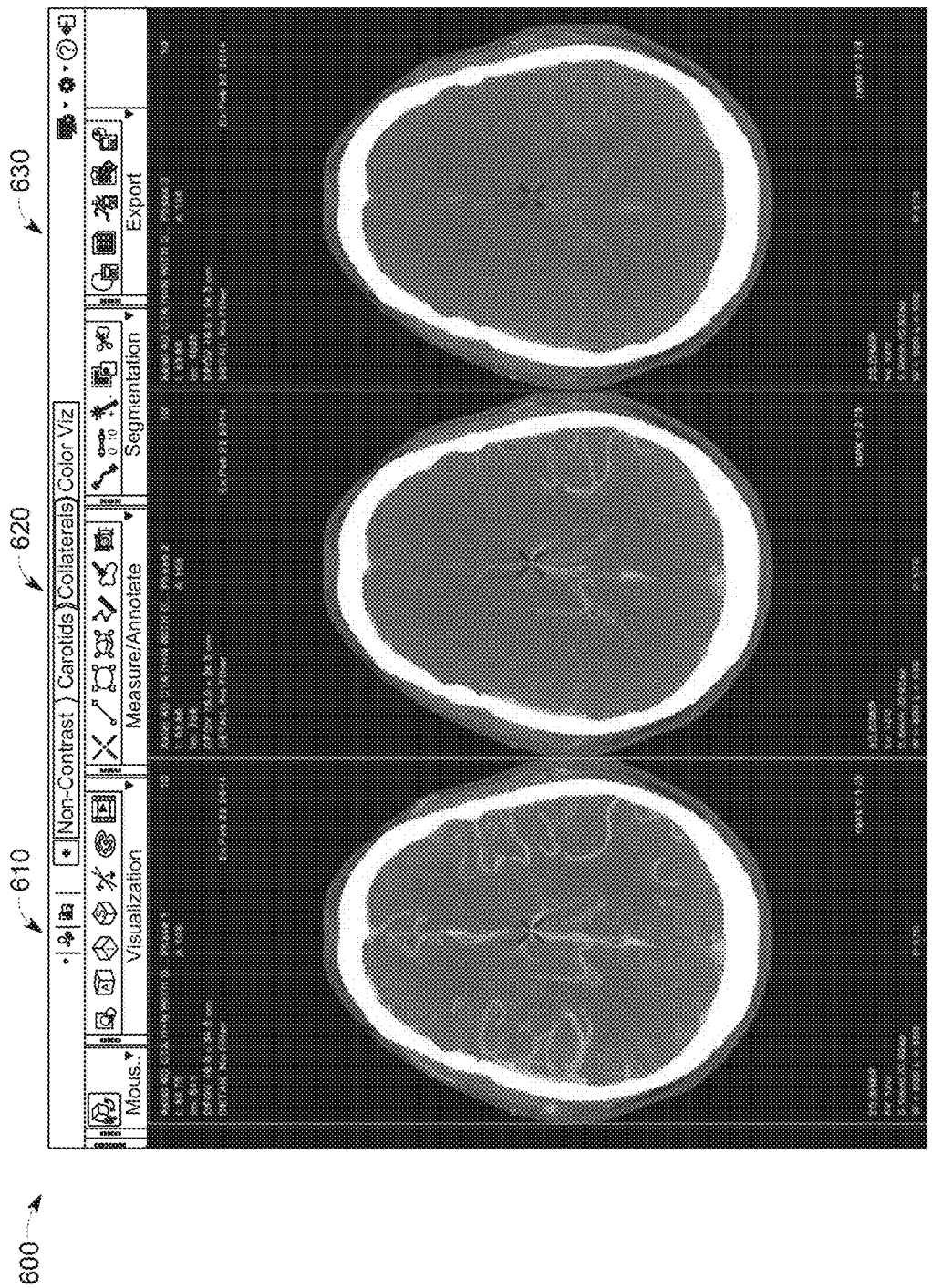
FIG. 6 illustrates an example display in accordance with various embodiments.

At 226, a second image is reconstructed. The first image is reconstructed using the second type of diagnostic imaging information acquired at 222. At 228, the reconstructed image is automatically postprocessed. For example, in various embodiments, a processing unit (e.g., processing unit 120) may postprocess the reconstructed second image using a predetermined postprocessing routine (e.g., postprocessing tailored for multi-phase CTA) based on the selected progressive imaging routine to provide a user with a convenient, easily usable display for determining if a stop criterion is satisfied. FIG. 5 illustrates an example CTA display 500, and FIG. 6 illustrates an example CTA display 600 in accordance with various embodiments. The processing unit 120, responsive to receiving the image reconstructed at 226, in various embodiments automatically performs postprocessing on the image reconstructed at 226 to prepare the display 500 and display 600 for use. The display 500 displays carotids as part of a maximum intensity projection (MIP) in three different views—a coronal view 510, an axial view 520, and a sagittal view 530. The display 600 displays three axial views at different times or phases—a first phase view 610, a second phase view 620, and third phase view 630. The display 500 and display 600 may be used by a viewer to determine if there is sufficient collateral filling. For example, if there is sufficient collateral filling, the patient may proceed to an endovascular procedure to remove a clot, but if not, an alternative course may be selected due to the risk of rupturing blood vessels due to a pressure change after clot removal.

At 230, the second image is analyzed to determine if a second stop criterion for terminating imaging is satisfied by the second image. The analysis in some embodiments may be performed by an operator or user viewing an image or images on a display (e.g., display unit 140). It may be noted that the display may be remote from other aspects of an imaging system, so that a physician not present at a scanning facility may determine if a stop criterion has been satisfied. In some embodiments, a processing unit (e.g., processing unit 120) may be configured to analyze one or more determinable parameters or objective measurements corresponding to a reconstructed image to determine if a stop criterion has been met. In the depicted embodiment, at 232, the first image is analyzed by a viewer of a display to determine if there is sufficient collateral filling to permit clot removal. It may be noted that a location of a clot to be removed may also be determined at 234 in various embodiments.

At 236, it is determined if the second stop criterion has been met or satisfied. If the second stop criterion is met, the method 200 proceeds to 238 and the imaging series is terminated. If the stop criterion is not met or satisfied, the method proceeds to 240. For example, if sufficient collateral filling is present, the patient may be transferred from the imaging device for treatment of the ischemic stroke (e.g., removal of an identified clot) immediately, without spending additional time performing scans. If, however, the level of collateral filling is not sufficient, or if it cannot be determined from the multi-phase CTA analysis if collateral filling is sufficient, additional imaging may be beneficial, for example, to determine the extent of collateral filling.

At 240, a third type of diagnostic imaging information is acquired. For example, in various embodiments, the third type of diagnostic imaging information is of the same, first modality as the first type and second type of diagnostic imaging information, is acquired with the same, first imaging unit, and has an increased level of acquisitional burden relative to the second type of diagnostic imaging information. In the illustrated embodiment, at 242, the third type of diagnostic imaging information is CT perfusion information. CTA may be understood as looking at vessels at a macro-level, and CT perfusion may provide additional complexity or detail by providing information regarding the patient at a tissue level. Tissue level parameters are calculated as part of a CT perfusion analysis in various embodiments to provide one or more quantitative measures to assist in determining a level of collateral filling. In the illustrated embodiment, a contrast agent is introduced in the patient before acquiring CT information as part of a CT perfusion imaging process. In various embodiments, the reconstruction and associated analysis regarding the second imaging information may be performed during a washout period of contrast agent used in acquiring the second imaging information. It may also be noted that, in various embodiments, the patient is maintained on a table of the first imaging unit during the acquiring of the second type of diagnostic imaging information, reconstructing of the second image, analyzing of the second image, and acquiring of the third type of diagnostic imaging information.

Figure 7:
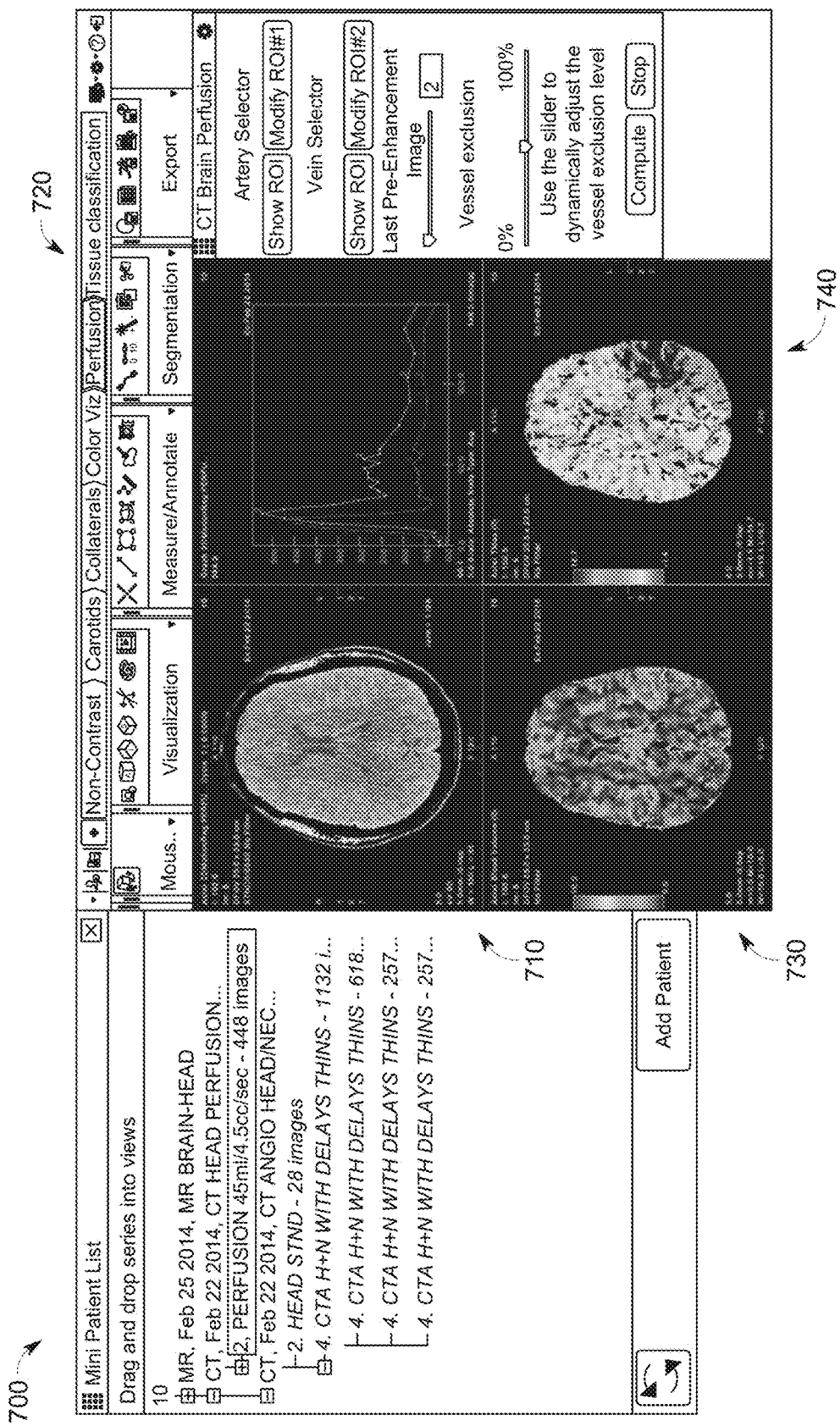
FIG. 7 illustrates an example display in accordance with various embodiments.

At 244, a third image is reconstructed. The third image is reconstructed using the third type of diagnostic imaging information acquired at 240. At 246, the reconstructed image is automatically postprocessed. For example, in various embodiments, a processing unit (e.g., processing unit 120) may postprocess the reconstructed third image using a predetermined postprocessing routine (e.g., postprocessing tailored for CT perfusion) based on the selected progressive imaging routine to provide a user with a convenient, easily usable display. FIG. 7 illustrates an example CT perfusion 700 in accordance with various embodiments. The processing unit 120, responsive to receiving the image reconstructed at 244, in various embodiments automatically performs postprocessing on the image reconstructed at 244 to prepare the display 700 for use. The display 700 includes image views, 710, 730, and 740, as well as graph 720 corresponding to one or more quantitative measures. The particular views presented and format of the presented views for the display 700 (and/or other displays discussed herein) in various embodiments is automatically selected by a processing unit, for example, based on predetermined viewer preferences. For example, responsive to receiving a given type of reconstructed image, the processing unit may automatically selected a predetermined postprocessing routine corresponding to the given type of reconstructed image to prepare a display for viewing.

At 248, the third image is analyzed (e.g., to determine if a stop criterion is met if any additional scans remain in the progressive imaging routine). The analysis in some embodiments may be performed by an operator or user viewing an image or images on a display (e.g., display unit 140). It may be noted that the display may be remote from other aspects of an imaging system, so that a physician not present at a scanning facility may determine if a stop criterion has been satisfied. In some embodiments, a processing unit (e.g., processing unit 120) may be configured to analyze one or more determinable parameters or objective measurements (e.g., one or more quantitative measures provided by a CT perfusion imaging process) corresponding to a reconstructed image to determine if a stop criterion has been met. In some embodiments, the third image is analyzed for collateral filling, and a corresponding stop criterion is if a sufficient amount of collateral filling is determined to allow the patient to be transferred to have surgery to remove a clot.

At 250, in the illustrated embodiment, a fourth imaging acquisition is performed. The fourth imaging acquisition in various embodiments uses a different, second modality than was used for the first, second, and third types of diagnostic information. For example, CT may be employed for the first, second, and third types of diagnostic information, but the fourth imaging acquisition may be performed using MM. In some embodiments, the fourth imaging acquisition, may be performed to provide additional complexity or detail to information previously acquired, while in other embodiments the fourth imaging acquisition may be used to provide information for a different anatomical structure or diagnosis. In various embodiments, the fourth imaging acquisition is performed only if a stop criterion corresponding to the third type of diagnostic imaging information is not satisfied.

It may be noted that a number of imaging stages or acquisitions (or potential imaging stages or acquisition) may vary in different embodiments. Generally, in some embodiments, each imaging stage or step includes an acquisition, a reconstruction, a display, an analysis, and a determination if a stop criterion has been met. The sequence may be repeated for each subsequent stage or step (e.g., using different imaging techniques) until a stop criterion is met.

Figure 8:
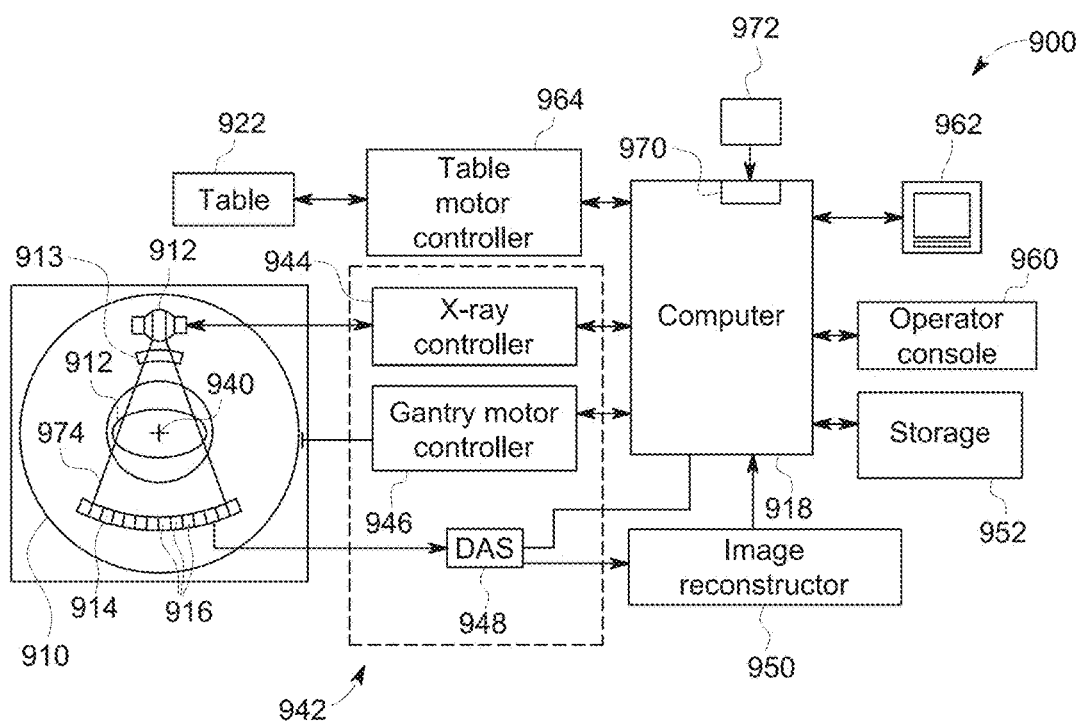
FIG. 8 is a schematic block diagram of an imaging system in accordance with various embodiments.

Various methods and/or systems (and/or aspects thereof) described herein may be implemented using a medical imaging system. For example, FIG. 8 is a block schematic diagram of an exemplary CT imaging system 900 that may be utilized to implement various embodiments discussed herein. Although the CT imaging system 900 is illustrated as a standalone imaging system, it should be noted that the CT imaging system 900 may form part of a multi-modality imaging system in some embodiments. For example, the multi-modality imaging system may include the CT imaging system 900 and a positron emission tomography (PET) imaging system, or a single photon emission computed tomography (SPECT) imaging system. It should also be understood that other imaging systems capable of performing the functions described herein are contemplated as being used.

The CT imaging system 900 includes a gantry 910 that has the X-ray source 912 that projects a beam of X-rays toward the detector array 914 on the opposite side of the gantry 910. A source collimator 913 and a bowtie filter module 915 are provided proximate the X-ray source 912. In various embodiments, the source collimator 913 may be configured to provide wide collimation as discussed herein. The detector array 914 includes a plurality of detector elements 916 that are arranged in rows and channels that together sense the projected X-rays that pass through a subject 917. The imaging system 900 also includes a computer 918 that receives the projection data from the detector array 914 and processes the projection data to reconstruct an image of the subject 917. The computer 918, for example, may include one or more aspects of the processing unit 120, or be operably coupled to one or more aspects of the processing unit 120. In operation, operator supplied commands and parameters are used by the computer 918 to provide control signals and information to reposition a motorized table 922. More specifically, the motorized table 922 is utilized to move the subject 917 into and out of the gantry 910. Particularly, the table 922 moves at least a portion of the subject 917 through a gantry opening (not shown) that extends through the gantry 910. Further, the table 922 may be used to move the subject 917 vertically within the bore of the gantry 910.

The depicted detector array 914 includes a plurality of detector elements 916. Each detector element 916 produces an electrical signal, or output, that represents the intensity of an impinging X-ray beam and hence allows estimation of the attenuation of the beam as it passes through the subject 917. During a scan to acquire the X-ray projection data, the gantry 910 and the components mounted thereon rotate about a center of rotation 940. FIG. 8 shows only a single row of detector elements 916 (i.e., a detector row). However, the multislice detector array 914 includes a plurality of parallel detector rows of detector elements 916 such that projection data corresponding to a plurality of slices can be acquired simultaneously during a scan.

Rotation of the gantry 910 and the operation of the X-ray source 912 are governed by a control mechanism 942. The control mechanism 942 includes an X-ray controller 944 that provides power and timing signals to the X-ray source 912 and a gantry motor controller 946 that controls the rotational speed and position of the gantry 910. A data acquisition system (DAS) 948 in the control mechanism 942 samples analog data from detector elements 916 and converts the data to digital signals for subsequent processing. An image reconstructor 950 receives the sampled and digitized X-ray data from the DAS 948 and performs high-speed image reconstruction. The reconstructed images are input to the computer 918 that stores the image in a storage device 952. The computer 918 may also receive commands and scanning parameters from an operator via a console 960 that has a keyboard. An associated visual display unit 962 allows the operator to observe the reconstructed image and other data from computer. It may be noted that one or more of the computer 918, controllers, or the like may be incorporated as part of a processing unit such as the processing unit 160 discussed herein.

The operator supplied commands and parameters are used by the computer 918 to provide control signals and information to the DAS 948, the X-ray controller 944 and the gantry motor controller 946. In addition, the computer 918 operates a table motor controller 964 that controls the motorized table 922 to position the subject 917 in the gantry 910. Particularly, the table 922 moves at least a portion of the subject 917 through the gantry opening.

In various embodiments, the computer 918 includes a device 970, for example, a CD-ROM drive, DVD drive, magnetic optical disk (MOD) device, or any other digital device including a network connecting device such as an Ethernet device for reading instructions and/or data from a tangible non-transitory computer-readable medium 972, that excludes signals, such as a CD-ROM, a DVD or another digital source such as a network or the Internet, as well as yet to be developed digital means. In another embodiment, the computer 918 executes instructions stored in firmware (not shown). The computer 918 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

In the exemplary embodiment, the X-ray source 912 and the detector array 914 are rotated with the gantry 910 within the imaging plane and around the subject 917 to be imaged such that the angle at which an X-ray beam 974 intersects the subject 917 constantly changes. A group of X-ray attenuation measurements, i.e., projection data, from the detector array 914 at one gantry angle is referred to as a "view" or "projection." A "scan" of the subject 917 comprises a set of views made at different gantry angles, or view angles, during one or more revolutions of the X-ray source 912 and the detector array 914. In a CT scan, the projection data is processed to reconstruct an image that corresponds to a three-dimensional volume taken of the subject 917. It may be noted that, in some embodiments, an image may be reconstructed using less than a full revolution of data. For example, with a multi-source system, substantially less than a full rotation may be utilized. Thus, in some embodiments, a scan (or slab) corresponding to a 360 degree view may be obtained using less than a complete revolution.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. An imaging system for progressively imaging a patient during a single patient visit comprising:
    an imaging unit of a first imaging modality, the first imaging modality comprising one of X-ray, computed tomography (CT), nuclear medicine imaging (NM), photon emission tomography (PET), single photon emission computed tomography (SPECT), or magnetic resonance imaging (MRI), the imaging unit comprising a detector;

a display unit configured to display reconstructed images; and at least one processor operably coupled to the imaging unit and the display unit, the at least one processor configured to:

acquire a first type of diagnostic imaging information of the patient from the first imaging modality with the imaging unit;

reconstruct a first image using the first type of diagnostic imaging information;

display the first image;

determine, based on the displayed first image, if a first stop criterion for terminating imaging is satisfied using the first image;

if the first stop criterion for terminating imaging is not satisfied, acquire a second type of diagnostic imaging information of the first imaging modality with the imaging unit, the second type of diagnostic imaging information having an increased level of acquisitional burden relative to the first type of diagnostic imaging information;

reconstruct a second image using the second type of diagnostic imaging information;

display the second image;

determine, based on the displayed second image, if a second stop criterion for terminating imaging is satisfied using the second image;

if the second stop criterion for terminating imaging is not satisfied, acquire a third type of diagnostic imaging information of the first imaging modality with the imaging unit, the third type of diagnostic imaging information having an increased level of acquisitional burden relative to the second type of diagnostic imaging information, wherein the patient is maintained on a table of the imaging unit during the acquisition of the second type of diagnostic imaging information, reconstruction of the second image, and acquisition of the third type of diagnostic imaging information, wherein the at least one processor is further configured to determine that one of the first stop criterion or second stop criterion is not satisfied if an input corresponding to a satisfaction of the one of the first stop criterion or second stop criterion is not received within a predetermined amount of time after displaying a corresponding image, wherein an absence of the input within the predetermined time results in additional imaging; and reconstruct a third image using the third type of diagnostic imaging information.

2. The imaging system of claim 1, further comprising a second imaging unit of a second modality that is different than the first modality, the second imaging unit comprising a second detector, wherein the at least one processor is configured to acquire additional imaging information using the second imaging unit after acquiring the third type of diagnostic imaging information.

3. The imaging system of claim 1, wherein the first type of diagnostic information is non-contrast computed tomography (CT) information, and the first stop criterion corresponds to a determination of a level of bleeding corresponding to hemorrhagic stroke.

4. The imaging system of claim 3, wherein the second type of diagnostic imaging information is multi-phase CT angiography (CTA) and the second stop criterion corresponds to determination of a sufficient level of collateral filling of blood vessels.

5. The imaging system of claim 4, wherein the third type of diagnostic imaging information is CT perfusion information.

6. The imaging system of claim 1, wherein the at least one processor is configured to automatically perform a predetermined postprocessing on the second type of diagnostic imaging information responsive to reconstructing the second type of diagnostic imaging information, and to perform a different predetermined postprocessing on the third type of diagnostic imaging information responsive to reconstructing the third type of diagnostic imaging information.

7. A method of progressively imaging a patient during a single patient visit, the method comprising:

acquiring a first type of diagnostic imaging information of the patient from a first imaging modality with a first imaging unit comprising a first detector, wherein the first imaging modality comprises one of X-ray, computed tomography (CT), nuclear medicine imaging (NM), photon emission tomography (PET), single photon emission computed tomography (SPECT), or magnetic resonance imaging (MRI);

reconstructing a first image using the first type of diagnostic imaging information;

displaying the first image;

determining, using the displayed first image, a first stop criterion for terminating imaging is not satisfied by the first image;

responsive to a determination that the first stop criterion has not been met, acquiring a second type of diagnostic imaging information of the first imaging modality with the first imaging unit, the second type of diagnostic imaging information having an increased level of acquisitional burden relative to the first type of diagnostic imaging information;

reconstructing a second image using the second type of diagnostic imaging information;

displaying the second image;

determining, using the displayed second image, a second stop criterion for terminating imaging is not satisfied by the second image;

responsive to a determination that the second stop criterion has not been met, acquiring a third type of diagnostic imaging information of the first imaging modality with the first imaging unit, the third type of diagnostic imaging information having an increased level of acquisitional burden relative to the second type of diagnostic imaging information, wherein the patient is maintained on a table of the first imaging unit during the acquiring the second type of diagnostic imaging information, reconstructing the second image, analyzing the second image, and acquiring the third type of diagnostic imaging information, wherein it is determined that one of the first stop criterion or second stop criterion is not satisfied if an input corresponding to a satisfaction of the one of the first stop criterion or second stop criterion is not received within a predetermined amount of time after displaying a corresponding image, wherein an absence of the input within the predetermined time results in additional imaging; and reconstructing a third image using the third type of diagnostic imaging information.

8. The method of claim 7, further comprising performing a subsequent imaging after acquiring the third type of diagnostic imaging information, the subsequent imaging using a second imaging modality that is different than the first imaging modality.

9. The method of claim 7, wherein the first type of diagnostic imaging information is non-contrast computed tomography (CT) information, and the first stop criterion is determination of a level of bleeding corresponding to hemorrhagic stroke.

10. The method of claim 9, wherein the second type of diagnostic imaging information is multi-phase CT angiography (CTA), and the second stop criterion is determination of a sufficient level of collateral filling of blood vessels.

11. The method of claim 10, further comprising determining a location of a clot using the second type of diagnostic imaging information.

12. The method of claim 10, wherein the third type of diagnostic imaging information is CT perfusion information.

13. The method of claim 7, further comprising automatically performing a predetermined postprocessing on the second type of diagnostic imaging information responsive to reconstructing the second type of diagnostic imaging information and a different predetermined postprocessing on the third type of diagnostic imaging information responsive to reconstructing the third type of diagnostic imaging information.

14. A tangible and non-transitory computer readable medium comprising one or more computer software modules configured to direct one or more processors to:
  acquire a first type of diagnostic imaging information of the patient from a first imaging modality with a first imaging unit comprising a first detector, wherein the first imaging modality comprises one of X-ray, computed tomography (CT), nuclear medicine imaging (NM), photon emission tomography (PET), single photon emission computed tomography (SPECT), or magnetic resonance imaging (MRI);
  reconstruct a first image using the first type of diagnostic imaging information;
  display the first image;
  determine, using the displayed first image, if a first stop criterion for terminating imaging is satisfied by the first image;
  responsive to a determination that the first stop criterion has been met, terminate imaging;
  responsive to a determination that the first stop criterion has not been met, acquire a second type of diagnostic imaging information of the first imaging modality with the first imaging unit, the second type of diagnostic imaging information having an increased level of acquisitional burden relative to the first type of diagnostic imaging information;
  reconstruct a second image using the second type of diagnostic imaging information;
  display the second image;
  determine, using the displayed second image if a second stop criterion for terminating imaging is satisfied by the second image;
  responsive to a determination that the second stop criterion has been met, terminate imaging;
  responsive to a determination that the second stop criterion has not been met, acquire a third type of diagnostic imaging information of the first imaging modality with the first imaging unit, the third type of diagnostic imaging information having an increased level of acquisitional burden relative to the second type of diagnostic imaging information, wherein the patient is maintained on a table of the first imaging unit during the acquiring the second type of diagnostic imaging information, reconstructing the second image, analyzing the second image, and acquiring the third type of diagnostic imaging information, wherein it is determined that one of the first stop criterion or second stop criterion is not satisfied if an input corresponding to a satisfaction of the one of the first stop criterion or second stop criterion is not received within a predetermined amount of time after displaying corresponding image, wherein an absence of the input within the predetermined time results in additional image; and
  reconstruct a third image using the third type of diagnostic imaging information.

15. The tangible and non-transitory computer readable medium of claim 14, wherein the first type of diagnostic imaging information is non-contrast computed tomography (CT) information, and the first stop criterion is determination of a level of bleeding corresponding to hemorrhagic stroke.

16. The tangible and non-transitory computer readable medium of claim 15, wherein the second type of diagnostic imaging information is multi-phase CT angiography (CTA), and the second stop criterion is determination of a sufficient level of collateral filling of blood vessels.

17. The tangible and non-transitory computer readable medium of claim 16, wherein the computer readable medium is further configured to determine a location of a clot using the second type of diagnostic imaging information.

18. The tangible and non-transitory computer readable medium of claim 17, wherein the third type of diagnostic imaging information is CT perfusion information.

19. The tangible and non-transitory computer readable medium of claim 14, wherein the computer readable medium is further configured to automatically performing a predetermined postprocessing on the second type of diagnostic imaging information responsive to reconstructing the second type of diagnostic imaging information and a different predetermined postprocessing on the third type of diagnostic imaging information responsive to reconstructing the third type of diagnostic imaging information.

* * * * *